United States Patent [19]

Heinemeyer et al.

[11] Patent Number: 4,794,180

[45] Date of Patent: Dec. 27, 1988

[54] PROCESS FOR PRODUCING FINE-GRAINED β-HMX

[75] Inventors: Klaus Heinemeyer, Leverkusen; Klaus Redecker, Nuremberg; Ulrich Sassmannshausen, Bruhl, all of Fed. Rep. of Germany

[73] Assignee: Dynamit Nobel Aktiengesellschaft, Troisdorf, Fed. Rep. of Germany

[21] Appl. No.: 53,480

[22] Filed: May 26, 1987

[30] Foreign Application Priority Data

May 23, 1986 [DE] Fed. Rep. of Germany ....... 3617408

[51] Int. Cl.$^4$ .................................... C07D 257/02
[52] U.S. Cl. .................................... 540/475
[58] Field of Search .................................... 540/475

[56] References Cited

U.S. PATENT DOCUMENTS

| 3,297,681 | 1/1967 | Wright et al. | 540/475 |
| 3,304,300 | 2/1967 | Watters | 540/475 |
| 4,638,065 | 1/1987 | Svensson et al. | 540/475 |

Primary Examiner—Glennon H. Hollrah
Assistant Examiner—D. B. Springer
Attorney, Agent, or Firm—Antonelli, Terry & Wands

[57] ABSTRACT

A process for producing fine-grained β-HMX wherein a solution of β-HMX is treated in a γ-lactone in a temperature range of between 5° and 15° C. with toluene, and the desired fine and very pure β-HMX crystals are precipitated. The resultant crystals have grain sizes of down to 5 μm and exhibit an extremely small proportion of other modifications or forms of HMX. An additional aspect of the process resides in providing the very fine β-HMX with a coating of a thermoplastic polymer. In this procedure, the β-HMX particles, after having been separated from toluene, are made into a slurry in water and combined under agitation at temperatures of between 25° and 60° C. with a solution or suspension or emulsion of the thermoplastic polymer. During this step, granules are formed which can be separated after distillation of the solvent.

8 Claims, No Drawings

PROCESS FOR PRODUCING FINE-GRAINED β-HMX

The present invention relates to a process for producing an especially fine-grained β-HMX wherein the crystals are precipitated from a β-HMX solution by means of a nonsolvent for β-HMX.

The explosive compound cyclotetramethylenetetranitramine, generally called HMX, exists in four different modifications of which only the β-form is stable at temperatures of up to 104° C. and thus has — under suitable safety measures—an unlimited shelf life. During its manufacture, it is obtained in grain sizes of about 50 μm ($10^{-6}$ m). However, for certain usages, β-HMX is needed in grain sizes of below 50 μm down to grain sizes of 2 μm so that it is necessary to find procedures for producing such a fine-grained β-HMX.

The rather obvious crushing of the crystals by grinding provides a problem in that β-HMX is extremely sensitive to friction and impact so that there is always the danger of explosion during mechanical comminution. Therefore, comminution may take place by means of special grinding processes. The thus-obtained crystals exhibit, however, the drawback that they have sharp fracture edges which edges, in turn, impair the safety characteristics of the product.

Therefore, the object of the present invention resides in finding a process for producing fine-grained β-HMX having grain sizes of below 50 μm wherein the above-mentioned safety risks are extensively precluded and wherein a product is obtained that can be warehoused while retaining its grain size.

In attainment of this object, a process has now been found for producing β-HMX by recrystallization of a solution containing β-HMX by means of a nonsolvent for β-octogen, characterized in that the recrystallization is performed from a solution of β-HMX in a γ-lactone with toluene in a temperature range of between 5° and 15° C., and that subsequently the thus-obtained crystals may be further processed in a conventional manner.

When conducting this procedure, a β-HMX is obtained having a very high purity with a content of other modifications or forms of HMX, especially of the α-form, of below 0.5% and having an average grain size of down to 5 μm. The yields in this process range at about 90%.

The β-HMX utilized as the starting compound need not have the high purity with respect to other modifications of HMX. Even if it contains, for example, 5% of the α- or some other modification, a product is obtained having the aforementioned purity.

Suitable solvents for β-HMX are, in principle, all γ-lactones which are liquid at room temperature and which exhibit solubility for β-HMX. A preferred lactone is γ-butyrolactone. If at all possible, dissolution of β-HMX in the lactones for producing the solutions to be used in the process of this invention is to be performed at temperatures of up to 50° C.

Precipitation with toluene is to take place in a temperature range of between 5° to 15° C. At this temperature, especially fine and very pure β-HMX crystals are obtained lying in a grain size range around 5 μm. At higher temperatures, the proportion of larger crystals is higher, or changes in modification occur.

A preferred way of performing the process for maintaining the precipitation temperature resides in allowing the β-HMX solution to drip as droplets into cooled toluene of the indicated temperature. During this step, the toluene is to be vigorously agitated. However, other ways of performing the process are also possible according to this invention, as long as maintenance of a temperature range from 5° to 15° C. is ensured. In general, the volume of toluene employed to promote precipitation should be at least twice the volume, and preferably three to six times more than the volume, of the solution of the HMX and the volume of the toluene can be as much as tenfold that of the HMX solution.

Separation and drying of the precipitated crystals takes place conventionally. The drying temperatures, however, should not exceed 50° C., if at all possible, since otherwise there is the danger of caking of the crystals.

In order to prevent caking of the fine crystals obtained according to the process, a further procedure of performing the process of this invention has been found which resides in that the resultant crystals, after having been separated from the toluene solution, are provided with a coating of synthetic resin. The procedure is carried out essentially as follows:

The separated β-HMX is made into a slurry with water and combined at temperatures of between 25° and 60° C. under agitation with a solution or emulsion or suspension of a thermoplastic polymer, thus bringing about the formation of granules; subsequently, the resultant granular dispersion is heated to temperatures of up to maximally 100° C. in order to remove the solvent for the polymer by distillation. The resultant granulated product shows a considerably lower shock and friction sensitivity than uncoated β-HMX. It shows good flowability, and the coated crystals do not tend to form agglomerates or lumps which can easily occur with the uncoated crystals.

Suitable thermoplastic polymers for the coating step are polyvinyl acetals obtained by reacting polyvinyl alcohol with aldehyde, such as, for example, polyvinyl butyral. Also acrylic resins can be utilized, such as, for example, methyl acrylate, methyl methacrylate or acrylonitrile resins. A preferred resin is polyvinyl butyral resin. The resin coating constitutes between 3 and 15% by weight of the coated crystals.

EXAMPLE 1

A solution was prepared at about 30° C. from 20 g of a commercially available β-HMX having an average grain size of 55 μm in 100 ml of γ-butyrolactone. This solution was gradually stirred into a provided quantity (one liter) of toluene at 8° to 15° C., thus bringing about precipitation; the resultant precipitate was filtered off, washed with water, and dried at temperatures of below 50° C. The yield was 90%. The average grain size of the thus-obtained product was < 6 μm, i.e. less than 6 μm and more than 2 μm, measured by means of a sedimentation measuring device "Analysette 20".

EXAMPLE 2

The starting compound employed was 40 g of a β-HMX having an average grain size of 55 μm with a γ-octogen content of 2%. Processing took place in accordance with Example 1. The resultant β-HMX likewise had an average grain size of <6 μm, measured as a dispersion in water by means of the sedimentation measuring device "Analysette 20." The γ-HMX content according to IR spectrometry was below 0.5% by weight.

What is claimed is:

1. A process for producing fine grained β-HMX by recrystallization of a solution containing β-HMX in a nonsolvent for β-HMX, characterized in that the recrystallization is conducted in a temperature range of between 5° and 50° C. by admixing a solution of β-HMX in a γ-lactone with toluene and subsequently the resulting crystals of β-HMX are recovered from the toluene; said crystals having a grain size between 2 μm and 50 μm.

2. A process according to claim 1, wherein the β-HMX solution is fed gradually into a provided quantity of toluene with agitation of the toluene.

3. A process according to claim 1, wherein the γ-lactone is γ-butyrolactone.

4. A process according to claim 2, wherein the γ-lactone is γ-butyrolactone.

5. A process according to claim 1, which further comprises providing the thus-obtained crystals, after their separation, with a synthetic resin coating.

6. A process according to claim 1, wherein the crystals recovered from the toluene are dried at a temperature not greater than 50° C.

7. A process according to claim 1, wherein the crystals recovered from the toluene have an α-HMX or γ-HMX content of less than 0.5% by weight.

8. A process according to claim 1, wherein the crystals recovered from the toluene have a grain size ranging from more than 2 μm to less than 6 μm.

* * * * *